United States Patent
Imada (10) Patent No.: US 10,466,590 B2
(45) Date of Patent: *Nov. 5, 2019

(54) NAPHTHOL-TYPE CALIXARENE COMPOUND AND METHOD FOR PRODUCING THE SAME, PHOTOSENSITIVE COMPOSITION, RESIST MATERIAL, AND COATING

(71) Applicant: DIC Corporation, Tokyo (JP)

(72) Inventor: Tomoyuki Imada, Ichihara (JP)

(73) Assignee: DIC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/516,736

(22) PCT Filed: Sep. 15, 2015

(86) PCT No.: PCT/JP2015/076096
§ 371 (c)(1),
(2) Date: Apr. 4, 2017

(87) PCT Pub. No.: WO2016/056355
PCT Pub. Date: Apr. 14, 2016

(65) Prior Publication Data
US 2017/0329226 A1   Nov. 16, 2017

(30) Foreign Application Priority Data
Oct. 10, 2014 (JP) .................. 2014-209265

(51) Int. Cl.
  G03F 7/039  (2006.01)
  G03F 7/004  (2006.01)
  C07C 37/16  (2006.01)
  C07C 39/14  (2006.01)

(52) U.S. Cl.
CPC ............ *G03F 7/0392* (2013.01); *C07C 37/16* (2013.01); *C07C 39/14* (2013.01); *G03F 7/0045* (2013.01)

(58) Field of Classification Search
None
See application file for complete search history.

(56) References Cited

U.S. PATENT DOCUMENTS

| | | | | |
|---|---|---|---|---|
| 4,551,508 A * | 11/1985 | Urasaki | ........... | C07D 303/24 |
| | | | | 525/481 |
| 5,166,173 A | 11/1992 | Hwang et al. | | |
| 5,196,452 A | 3/1993 | Hwang et al. | | |
| 5,302,672 A | 4/1994 | Ogura et al. | | |
| 5,302,673 A * | 4/1994 | Naka | ........... | C08G 8/08 |
| | | | | 525/481 |
| 9,828,457 B2 | 11/2017 | Imada et al. | | |
| 9,975,830 B2 * | 5/2018 | Imada | ........... | C07C 39/14 |
| 2004/0077804 A1 * | 4/2004 | Kamata | ........... | C08F 2/002 |
| | | | | 526/74 |
| 2010/0028802 A1 | 2/2010 | Konno et al. | | |
| 2010/0316950 A1 | 12/2010 | Oguro et al. | | |
| 2012/0171631 A1 | 7/2012 | Ideno et al. | | |
| 2012/0270157 A1 | 10/2012 | Minegishi et al. | | |
| 2012/0285929 A1 | 11/2012 | Matsumura et al. | | |
| 2012/0308832 A1 * | 12/2012 | Satou | ........... | C08G 8/08 |
| | | | | 428/414 |

(Continued)

FOREIGN PATENT DOCUMENTS

JP    61-069826 A    4/1986
JP    61-138622 A    6/1986

(Continued)

OTHER PUBLICATIONS

International Search Report dated Dec. 15, 2015, issued in counterpart International Application No. PCT/JP2015/076096 (2 pages).
International Search Report dated Feb. 9, 2016, issued in International Application No. PCT/JP2015/082513.
Office Action dated Feb. 26, 2019, issued in counterpart CN application No. 201580055065.9, with Japanese translation. (13 pages).
Hiraoka, H.: "Functionally Substituted Novolak Resins: Lithographic Applications, Radiation Chemistry, and Photooxidation", ACS Symposium Series, 1984, pp. 339-360, cited in CN Office Action dated Feb. 26, 2019 (22 pages).

(Continued)

*Primary Examiner* — Martin J Angebranndt
(74) *Attorney, Agent, or Firm* — Westerman, Hattori, Daniels & Adrian, LLP (57) ABSTRACT

Provided are a naphtol-type calixarene compound having high solvent solubility, a method for producing the naphthol-type calixarene compound, a photosensitive composition that contains the naphthol-type calixarene compound and provides a coating having high thermal decomposition resistance, alkali developability, photosensitivity, and resolution, and a resist material and a coating each being made of the photosensitive composition. Specifically, provided is a naphthol-type calixarene compound including a molecular structure represented by general formula (1). [In the formula (1), $R^1$ represents a hydrogen atom, an alkyl group, an alkoxy group, an optionally substituted aryl group, an optionally substituted aralkyl group, or a halogen atom, and a plurality of $R^1$ may be the same or different from each other; $R^2$ represents an optionally substituted alkyl group or an optionally substituted aryl group; and n represents an integer of 2 to 10].

[Chem. 1]

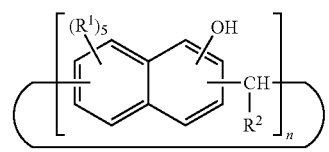

(1)

5 Claims, 1 Drawing Sheet

(56) References Cited

U.S. PATENT DOCUMENTS

| | | | |
|---|---|---|---|
| 2013/0078569 A1 | 3/2013 | Jain et al. | |
| 2013/0098870 A1 | 4/2013 | Wakamatsu et al. | |
| 2013/0157195 A1 | 6/2013 | Green et al. | |
| 2014/0186776 A1 | 7/2014 | Uchiyama et al. | |
| 2015/0185613 A1* | 7/2015 | Toyokawa | G03F 7/26 438/704 |
| 2016/0177020 A1 | 6/2016 | Imada et al. | |
| 2017/0066703 A1* | 3/2017 | Imada | C07C 39/14 |
| 2017/0082923 A1* | 3/2017 | Imada | G03F 7/023 |
| 2017/0329226 A1 | 11/2017 | Imada | |
| 2017/0334817 A1* | 11/2017 | Imada | C07C 39/14 |

FOREIGN PATENT DOCUMENTS

| | | | | |
|---|---|---|---|---|
| JP | 2-189326 A | | 7/1990 | |
| JP | H05132543 A | | 5/1993 | |
| JP | 06-135871 | * | 5/1994 | ............ C07C 39/15 |
| JP | 10-239843 A | | 9/1998 | |
| JP | 2010-248435 A | | 11/2010 | |
| JP | 2010-277061 | * | 12/2010 | ............ G03F 7/004 |
| JP | 2012-162474 A | | 8/2012 | |
| JP | 2012-201798 A | | 10/2012 | |
| JP | 2012-252323 A | | 12/2012 | |
| JP | 2013-067697 | * | 4/2013 | ............ C08G 59/62 |
| JP | 2013-173839 | * | 9/2013 | ............ C08G 10/02 |
| JP | 2013-181164 | * | 9/2013 | ............ C08G 8/32 |
| WO | 97/15566 | * | 5/1997 | ............ C07D 339/00 |
| WO | 2012/165507 A1 | | 12/2012 | |
| WO | 2014/038680 | * | 3/2014 | ............ G03F 7/26 |
| WO | 2017/098881 | * | 6/2017 | ............ G03F 7/039 |
| WO | 2017/098882 | * | 6/2017 | ............ G03F 7/004 |

OTHER PUBLICATIONS

International Search Report and Written Opinion dated Sep. 9, 2014, issued in coounterpart Application No. PCT/JP2014/065573 (5 pages).

* cited by examiner

FIG. 1

[minutes]

FIG. 2

[minutes]

NAPHTHOL-TYPE CALIXARENE COMPOUND AND METHOD FOR PRODUCING THE SAME, PHOTOSENSITIVE COMPOSITION, RESIST MATERIAL, AND COATING

TECHNICAL FIELD

The present invention relates to a naphthol-type calixarene compound having high solvent solubility, a method for producing the naphthol-type calixarene compound, a photosensitive composition that contains the naphthol-type calixarene compound and provides a coating having high thermal decomposition resistance, alkali developability, photosensitivity, and resolution, and a resist material and a coating each being made of the photosensitive composition.

BACKGROUND ART

Phenolic hydroxyl-containing compounds have been used for adhesives, molding materials, paints, photoresist materials, epoxy resin raw materials, curing agents for epoxy resins, and others. In addition, phenolic hydroxyl-containing compounds, when cured, have high heat resistance, high moisture resistance, and other excellent properties, and thus have been widely used in the form of curable resin compositions containing phenolic hydroxyl-containing compounds as main components and used as curing agents for epoxy resins and for others, in electrical and electronic applications such as semiconductor sealing materials and insulating materials for printed wiring boards.

For resin materials for positive photoresists among the above applications, resin compositions containing a novolac phenol resin, which has high heat resistance and alkali solubility, and a sensitizer such as a naphthoquinone diazide compound have been widely used, and recent miniaturization of circuit patterns has necessitated higher photosensitivity and resolution. In addition, higher thermal decomposition resistance is also required because various heat treatments are performed in the process for manufacturing semiconductors and others. That is to say, novel photoresist resin materials having sensitivity and thermal decomposition resistance both at high levels should be developed.

Positive photoresists containing an alkali-soluble resin and a sensitizer such as a 1,2-naphthoquinone diazide compound are known as resists used to manufacture semiconductors, such as ICs and LSIs, display devices, such as LCDs, original printing plates, and others. For example, phenolic hydroxyl-containing compounds having high thermal decomposition resistance are known, such as a dihydroxynaphthalene-type novolac resin (see PTL 1) and a phenolic hydroxyl-containing compound having a tubular structure called a calixarene structure (a calixarene compound) (see PTL 2).

CITATION LIST

Patent Literature

PTL 1: Japanese Unexamined Patent Application Publication No. 2010-248435
PTL 2: Japanese Unexamined Patent Application Publication No. 2012-162474

SUMMARY OF INVENTION

Technical Problem

The dihydroxynaphthalene-type novolac resin described in PTL 1, among commonly-used phenol novolac resins, has high thermal decomposition resistance, but further improvements are needed to satisfy the recent increasing demand for thermal decomposition resistance. In addition, the dihydroxynaphthalene-type novolac resin, when used in resist applications, may provide insufficient sensitivity and resolution. The calixarene compound described in PTL 2 is insufficiently soluble in common organic solvents and thus is difficult to apply in adhesive, paint, photoresist, and printed wiring board applications.

Thus, it is an object of the present invention to provide a naphthol-type calixarene compound having high solvent solubility, a method for producing the naphthol-type calixarene compound, a photosensitive composition that contains the naphthol-type calixarene compound and provides a coating having high thermal decomposition resistance, alkali developability, photosensitivity, and resolution, and a resist material and a coating each being made of the photosensitive composition.

Solution to Problem

The inventor conducted intensive studies to solve the above-described problem and found that a hydroxynaphthalene-type calixarene compound has significantly high thermal decomposition resistance and is highly soluble in common solvents, that the calixarene compound is obtained by reacting a hydroxynaphthalene with an aliphatic or aromatic aldehyde in the presence of an acid catalyst, that a photosensitive composition obtained by using the calixarene compound provides a coating having high alkali developability, photosensitivity, and resolution as well as high thermal decomposition resistance, and that the photosensitive composition is suitable for use as a resist material for forming a resist coating, thereby completing the present invention.

Thus, the present invention relates to a naphthol-type calixarene compound having a molecular structure represented by the following general formula (1).

[Chem. 1]

(1)

(In the formula (1), $R^1$ represents a hydrogen atom, an alkyl group, an alkoxy group, an optionally substituted aryl group, an optionally substituted aralkyl group, or a halogen atom, and a plurality of $R^1$ may be the same or different from each other.)

$R^2$ represents an optionally substituted alkyl group or an optionally substituted aryl group; and n represents an integer of 2 to 10.)

The present invention further relates to a method for producing a naphthol-type calixarene compound, including reacting a hydroxynaphthalene (A) represented by the following general formula (2) with an aldehyde (B) represented by the following general formula (3) in the presence of an acid catalyst to obtain the naphthol-type calixarene compound.

[Chem. 2]

(2)

(In the formula (2), $R^1$ represents a hydrogen atom, an alkyl group, an alkoxy group, an optionally substituted aryl group, an optionally substituted aralkyl group, or a halogen atom, and a plurality of $R^1$ may be the same or different from each other.)

[Chem. 3]

$$R^2\text{—CHO} \quad (3)$$

(In the formula (3), $R^2$ represents an optionally substituted alkyl group or an optionally substituted aryl group.)

The present invention further relates to a photosensitive composition containing the above-described naphthol-type calixarene compound or a naphthol-type calixarene compound, produced by the above-described method for producing a naphthol-type calixarene compound, and a sensitizer.

The present invention further relates to a resist material made of the photosensitive composition and a coating made of the photosensitive composition.

Advantageous Effects of Invention

The naphthol-type calixarene compound according to the present invention has high solvent solubility and coating properties. Applying a photosensitive composition containing the naphthol-type calixarene compound provides a coating having high thermal decomposition resistance, alkali developability, photosensitivity, and resolution, and thus the photosensitive composition is suitable particularly as a photosensitive composition for resist materials and for others.

DESCRIPTION OF EMBODIMENTS

A naphthol-type calixarene compound according to the present invention is characterized by having a molecular structure represented by the following general formula (1). The naphthol-type calixarene compound, because of having a cyclic structure, has very high thermal decomposition resistance and is highly interactive with sensitizers.

[Chem. 4]

(1)

In the molecular structure represented by the general formula (1), the phenolic hydroxyl group in the naphthylene skeleton may be at any position. To provide a compound having high resolution and thermal decomposition resistance, the phenolic hydroxyl group is preferably at the 1 position. That is to say, the naphthol-type calixarene compound according to the present invention preferably has a molecular structure represented by the following general formula (1-1). In the general formula (1-1), $R^1$, $R^2$ and n are as defined in the general formula (1).

[Chem. 5]

(1-1)

In the general formula (1), $R^1$ represents a hydrogen atom, an alkyl group, an alkoxy group, an optionally substituted aryl group, an optionally substituted aralkyl group, or a halogen atom. In the naphthylene skeleton of the formula (1), the number of $R^1$ is 5, and the plurality of $R^1$ may be the same or different from each other.

When $R^1$ in the general formula (1) is an alkyl group, the alkyl group may be linear or branched, or may be a group having a cyclic structure, and is preferably a linear group. In the present invention, when $R^1$ is an alkyl group, to provide a naphthol-type calixarene compound having high solvent solubility and provide a coating having high thermal decomposition resistance, alkali developability, photosensitivity, and resolution, and also in terms of industrial availability, $R^1$ is preferably an alkyl group of 1 to 12 carbon atoms, more preferably an alkyl group of 1 to 8 carbon atoms, still more preferably an alkyl group of 1 to 6 carbon atoms. Specifically, the alkyl group may be methyl, ethyl, propyl, isopropyl, n-butyl, isobutyl, t-butyl, pentyl, isoamyl, hexyl, cyclohexyl, heptyl, cyclohexylmethyl, octyl, cyclohexylethyl, nonyl, decyl, adamantyl, undecyl, adamantylmethyl, dodecyl, or adamantylethyl. The alkyl group is preferably methyl, ethyl, propyl, isopropyl, n-butyl, isobutyl, t-butyl, pentyl, isoamyl, hexyl, or cyclohexyl.

When $R^1$ in the general formula (1) is an alkoxy group, the alkyl moiety in the alkoxy group may be linear or branched, or may be a group having a cyclic structure, and is preferably a linear group. In the present invention, when $R^1$ is an alkoxy group, to provide a naphthol-type calixarene compound having high solvent, solubility and provide a coating having high thermal decomposition resistance, alkali developability, photosensitivity, and resolution, and also in terms of industrial availability, $R^1$ is preferably an alkoxy group of 1 to 12 carbon atoms, more preferably an alkoxy group of 1 to 8 carbon atoms, still more preferably an alkoxy group of 1 to 6 carbon atoms. Specifically, the alkoxy group may be methoxy, ethoxy, propyloxy, isopropyloxy, n-butyloxy, isobutyloxy, t-butyloxy, pentyloxy, isoamyloxy, hexyloxy, clohexyloxy, heptyloxy, octyloxy, nonyloxy, decyloxy, undecyloxy, or dodecyloxy. The alkoxy group is preferably methoxy, ethoxy, propyloxy, butyloxy, pentyloxy, hexyloxy, or cyclohexyloxy.

When $R^1$ in the general formula (1) is an optionally substituted aryl group, examples of the aryl group include phenyl, naphthyl, indenyl, and biphenyl. Hydrogen in the aryl group may be substituted with a substituent, and examples of the substituent include a hydroxyl group, alkyl groups of 1 to 6 carbon atoms, and alkoxy groups of 1 to 6 carbon atoms. The number of substituents in the aryl group is preferably, but not necessarily, 1 to 3, more preferably 1 or 2. When one aryl group has two or more substituents, the substituents may be the same or different from each other. Specifically, to provide a naphthol-type calixarene compound having high solvent solubility and provide a coating having high thermal decomposition resistance, alkali developability, photosensitivity, and resolution, and also in terms of industrial availability, the optionally substituted aryl group may be, for example, phenyl, hydroxyphenyl, dihydroxyphenyl, hydroxyalkoxyphenyl, alkoxyphenyl, tolyl, xylyl, naphthyl, hydroxynaphthyl, or dihydroxynaphthyl, and is preferably phenyl.

When $R^1$ in the general formula (1) is an optionally substituted aralkyl group, examples of the aryl moiety in the aralkyl group include phenyl, naphthyl, indenyl, and biphenyl, and phenyl is preferred. The alkyl moiety in the aralkyl group may be linear or branched, or may be a group having a cyclic structure, and is preferably a linear group, more preferably an alkyl group of 1 to 6 carbon atoms, still more preferably a linear or branched alkyl group of 1 to 6 carbon atoms. Hydrogen in the aryl moiety in the aralkyl group may be substituted with a substituent, and the type and the number of the substituent are the same as those of the optional substituent on the aryl group. Specific examples of the optionally substituted aralkyl group include phenylmethyl, hydroxyphenylmethyl, dihydroxyphenylmethyl, tolylmethyl, xylylmethyl, naphthylmethyl, hydroxynaphthylmethyl, dihydroxynaphthylmethyl, phenylethyl, hydroxyphenylethyl, dihydroxyphenylethyl, tolylethyl, xylylethyl, naphthylethyl, hydroxynaphthylethyl, and dihydroxynaphthylethyl. To provide a naphthol-type calixarene compound having high solvent solubility and provide a coating having high thermal decomposition resistance, alkali developability, photosensitivity, and resolution, and also in terms of industrial availability, the optionally substituted aralkyl group is preferably phenylmethyl, hydroxyphenylmethyl, or dihydroxyphenylmethyl.

When $R^1$ in the general formula (1) is a halogen atom, examples of the halogen atom include fluorine, chlorine, and bromine.

In the molecular structure represented by the general formula (1), to provide a naphthol-type calixarene compound having high solvent solubility and provide a coating having high thermal decomposition resistance, alkali developability, photosensitivity, and resolution, and also in terms of industrial availability of raw materials, $R^1$ is preferably a hydrogen atom, an alkyl group, or an alkoxy group. In particular, to provide an compound having high thermal decomposition resistance and water absorption resistance, it is more preferred that all $R^1$ be hydrogen atoms or alkyl groups; it is still more preferred that all $R^1$ be hydrogen atoms, methyl groups, ethyl groups, propyl groups, isopropyl groups, n-butyl groups, isobutyl groups, t-butyl groups, pentyl groups, isoamyl groups, hexyl groups, or cyclohexyl groups; it is yet more preferred that all $R^1$ be hydrogen atoms, methyl groups, ethyl groups, propyl groups, isopropyl groups, n-butyl groups, isobutyl groups, or t-butyl groups; and it is particularly preferred that all $R^1$ be hydrogen atoms.

$R^2$ in the general formula (1) represents an optionally substituted alkyl group or an optionally substituted aryl group.

When $R^2$ in the general formula (1) is an optionally substituted alkyl group, the alkyl group may be linear or branched, or may be a group having a cyclic structure, and is preferably a linear group to provide a naphthol-type calixarene compound having high solvent solubility and provide a coating having high thermal decomposition resistance, alkali developability, photosensitivity, and resolution, and also in terms of industrial availability of raw materials. In the present invention, when $R^2$ is an alkyl group, $R^2$ is preferably an alkyl group of 1 to 12 carbon atoms, more preferably an alkyl group of 1 to 8 carbon atoms, still more preferably an alkyl group of 1 to 6 carbon atoms.

When $R^2$ in the general formula (1) is an alkyl group, hydrogen in the alkyl group may be substituted with a substituent. Examples of the substituent include a hydroxyl group, alkoxy groups of 1 to 6 carbon atoms, optionally substituted aryl groups, and halogen atoms. Examples of the alkoxy groups of 1 to 6 carbon atoms include the same groups as listed as the examples of alkoxy groups of $R^1$, and examples of the aryl groups include the same groups as listed as the examples of aryl groups of $R^1$. The number of hydrogen atoms that can be substituted is preferably, but not necessarily, 1 to 3, more preferably 1 or 2. When one alkyl group has two or more substituents, the substituents may be the same or different from each other. Specific examples of the alkyl group of $R^2$ include methyl, ethyl, propyl, isopropyl, n-butyl, isobutyl, t-butyl, pentyl, isoamyl, hexyl, cyclohexyl, hydroxyethyl, hydroxypropyl, fluoromethyl, methoxyethyl, ethoxyethyl, methoxypropyl, phenylmethyl, hydroxyphenylmethyl, dihydroxyphenylmethyl, tolylmethyl, xylylmethyl, naphthylmethyl, hydroxynaphthylmethyl, dihydroxynaphthylmethyl, phenylethyl, hydroxyphenylethyl, dihydroxyphenylethyl, tolylethyl, xylylethyl, naphthylethyl, hydroxynaphthylethyl, and dihydroxynaphthylethyl. To provide a coating having high dry etching resistance and thermal decomposition resistance and provide a photosensitive composition having high sensitivity and resolution, the alkyl group of $R^2$ is preferably methyl, ethyl, propyl, isopropyl, n-butyl, isobutyl, t-butyl, pentyl, isoamyl, hexyl, or cyclohexyl, more preferably methyl.

When $R^2$ in the general formula (1) is an optionally substituted aryl group, examples of the aryl group include phenyl, naphthyl, indenyl, and biphenyl. Hydrogen in the aryl group may be substituted with a substituent. Examples of the substituent include a hydroxyl group, alkoxy groups of 1 to 6 carbon atoms, aryl groups, and halogen atoms. Examples of the alkoxy groups of 1 to 6 carbon atoms include the same groups as listed as the examples of alkoxy groups of $R^1$, and examples of the aryl groups include the same groups as listed as the examples of aryl groups of $R^1$. The number of hydrogen atoms that can be substituted is preferably, but not necessarily, 1 to 3, more preferably 1 or 2. When one aryl group has two or more substituents, the substituents may be the same or different from each other. Specific examples of the optionally substituted aryl group of $R^2$ include phenyl, hydroxyphenyl, dihydroxyphenyl, hydroxyalkoxyphenyl, alkoxyphenyl, tolyl, xylyl, naphthyl, hydroxynaphthyl, dihydroxynaphthyl, and bromphenyl.

In the molecular structure represented by the general formula (1), to provide a coating having high dry etching resistance and thermal decomposition resistance and provide a photosensitive composition having high sensitivity and resolution, $R^2$ is preferably an optionally substituted aryl group, more preferably a hydroxyl-containing aryl group, such as a hydroxyphenyl group, a dihydroxyphenyl group, a hydroxyalkoxyphenyl group, a hydroxynaphthyl group, or a dihydroxynaphthyl group, still more preferably a hydroxyphenyl group.

In the general formula (1), n represents the number of repeating units and is an integer of 2 to 10. In particular, to provide a naphthol-type calixarene compound that provides a coating having high structural stability and thermal decomposition resistance, n is preferably any one of 2, 3, 4, 5, 6, and 8, particularly preferably 4.

The naphthol-type calixarene compound according to the present invention is obtained by reacting a hydroxynaphthalene (A) represented by the following general formula (2) with an aldehyde (B) represented by the following general formula (3). In the general formula (2), $R^1$ is as defined in the above general formula (1). In the general formula (3), $R^2$ is as defined in the above general formula (1).

[Chem. 6]

(2)

(3)

The hydroxynaphthalene (A) may be any compound represented by the above general formula (2). Examples include 1-naphthol, 2-naphthol, and derivatives thereof whose aromatic nuclei are substituted with one or more alkyl groups, alkoxy groups, aryl groups, aralkyl groups, and halogen atoms, among which 1-naphthol and 2-naphthol are preferred, and 1-naphthol is particularly preferred. The hydroxynaphthalene (A) for use as a raw material may be a single compound or a combination of two or more compounds.

The aldehyde (B) may be any compound represented by the above general formula (3). In particular, the aldehyde (B) is preferably alkyl aldehyde such as acetaldehyde, propylaldehyde, butyraldehyde, isobutyraldehyde, pentylaldehyde, or hexylaldehyde; hydroxybenzaldehyde such as salicylaldehyde, 3-hydroxybenzaldehyde, 4-hydroxybenzaldehyde, 2-hydroxy-4-methylbenzaldehyde, 2,4-dihydroxybenzaldehyde, or 3,4-dihydroxybenzaldehyde; benzaldehyde having both hydroxyl and alkoxyl such as 2-hydroxy-3-methoxybenzaldehyde, 3-hydroxy-4-methoxybenzaldehyde, 4-hydroxy-3-methoxybenzaldehyde, 3-ethoxy-4-hydroxybenzaldehyde, or 4-hydroxy-3,5-dimethoxybenzaldehyde; alkoxybenzaldehyde such as methoxybenzaldehyde or ethoxybenzaldehyde; hydroxynaphthoaldehyde such as 1-hydroxy-2-naphthoaldehyde, 2-hydroxy-1-naphthoaldehyde, or 6-hydroxy-2-naphthoaldehyde; halogenated benzaldehyde such as brombenzaldehyde; or others. The aldehyde (B) is more preferably acetaldehyde, propylaldehyde, 4-hydroxy-3-methoxybenzaldehyde, 3-ethoxy-4-hydroxybenzaldehyde, salicylaldehyde, 3-hydroxybenzaldehyde, 4-hydroxybenzaldehyde, or 2,4-dihydroxybenzaldehyde, still more preferably acetaldehyde, propylaldehyde, salicylaldehyde, 3-hydroxybenzaldehyde, or 4-hydroxybenzaldehyde, yet more preferably acetaldehyde, 3-hydroxybenzaldehyde, or 4-hydroxybenzaldehyde. The aldehyde (B) for use as a raw material may be a single compound or a combination of two or more compounds.

To efficiently produce a naphthol-type calixarene compound, the hydroxynaphthalene (A) and the aldehyde (B) are preferably reacted in a molar ratio [(A)/(B)] in the range of 0.5 to 1.5. A reaction of the hydroxynaphthalene (A) and the aldehyde (B) in a ratio within this range can produce a naphthol-type calixarene compound with a small amount of residual unreacted hydroxynaphthalene (A).

The reaction of the hydroxynaphthalene (A) with the aldehyde (B) may be carried out in an organic solvent or in a mixed solvent of water and an organic solvent. Examples of the organic solvent for use in the reaction include alcohols such as 2-ethoxyethanol, propanol, butanol, octanol, ethylene glycol, glycerol, ethylene glycol monomethyl ether, ethylene glycol monoethyl ether, ethylene glycol monobutyl ether, and propylene glycol monomethyl ether; ketones such as methyl ethyl ketone and methyl isobutyl ketone; and esters such as butyl acetate, ethylene glycol monomethyl ether acetate, ethylene glycol monoethyl ether acetate, and propylene glycol monomethyl ether acetate. The organic solvent for use in the reaction may be a single solvent or a mixed solvent of two or more solvents. In particular, it is preferable to use at least one selected from the group consisting of 2-ethoxyethanol, butanol, octanol, methyl ethyl ketone, and methyl isobutyl ketone.

When a mixed solvent of water and an organic solvent is used for the reaction, the amount of organic solvent used in the mixed solvent is preferably such that the amount of organic solvent is 50 to 500 parts by mass based on 100 parts by mass of the hydroxynaphthalene (A), because such conditions allow the reaction to proceed at a sufficiently high rate to efficiently produce a naphthol-type calixarene compound, and allow the solvent to be removed by distillation relatively in a short time after the production of the naphthol-type calixarene compound, and for other reasons. The amount of organic solvent is more preferably 100 to 500 parts by mass. The amount of water used in the mixed solvent is 30 to 300 parts by mass based on 100 parts by mass of the hydroxynaphthalene (A). The presence of plenty of water in the reaction system provides a naphthol-type calixarene compound with a low molecular weight, regardless of how low the molecular weight is, and with a small amount of residual monomer (the hydroxynaphthalene (A)). The amount of water in the reaction system is more preferably 35 to 250 parts by mass based on 100 parts by mass of the hydroxynaphthalene (A).

Examples of the acid catalyst for use in the reaction include inorganic acids such as sulfuric acid, hydrochloric acid, nitric acid, hydrobromic acid, perchloric acid, and phosphoric acid; organic acids such as sulfonic acids, including p-toluenesulfonic acid, methanesulfonic acid, and benzenesulfonic acid, oxalic acid, succinic acid, malonic acid, monochloacetic acid, and dichloroacetic acid; and Lewis acids such as boron trifluoride, anhydrous aluminum chloride, and zinc chloride. Of these, sulfuric acid, hydrochloric acid, nitric acid, and p-toluenesulfonic acid, which are strongly acidic and very actively promote the reaction between the hydroxynaphthalene (A) and the aldehyde (B), are preferred, and sulfuric acid is more preferred. The amount of acid catalyst for use is preferably in the range of 0.1% to 25% by mass based on the total mass of the reactants.

For high reaction efficiency, the hydroxynaphthalene (A) and the aldehyde (B) are preferably reacted at a temperature in the range of 50° C. to 120° C. Particularly when the hydroxynaphthalene (A) is 1-naphthol, the reaction is preferably carried out at 60° C. to 90° C.

The reaction between the hydroxynaphthalene (A) and the aldehyde (B) can be carried out, for example, as described below. First, the hydroxynaphthalene (A), an organic solvent, the aldehyde (B), and an acid catalyst are placed in a flask equipped with a thermometer, a condenser, a fractionating column, and a stirrer. The amount of acid catalyst for use is typically 0.01 to 5 parts by mass based on 100 parts by mass of the hydroxynaphthalene (A). The acid catalyst may be used in an amount above this range, but such an amount of acid catalyst will necessitate a large amount of alkali and extra time for a neutralization process. Thus, the amount of acid catalyst may be appropriately determined.

The reaction system is heated to a reaction temperature and then stirred to cause the hydroxynaphthalene (A) to react with the aldehyde (B). The reaction is typically carried out for 0.5 to 36 hours. After completion of the reaction, water and an organic solvent that will be phase separated from water (e.g., a hydrophobic organic solvent) are added, and as a result a naphthol-type calixarene compound obtained by the reaction and the hydroxynaphthalene (A) left unreacted are dissolved or dispersed in an organic solvent phase, and the aldehyde (B) left unreacted is dissolved or dispersed in an aqueous phase. The organic solvent phase and the aqueous layer in the reaction system, if stirred, will not be "uniformly" mixed (dissolved) but will be in an "ununiform" state. The two layers preferably form such an "ununiform" state. Part of the organic layer may be "uniformly" mixed with the aqueous layer, or part of the aqueous layer may be "uniformly" mixed with the organic layer. Part of the naphthol-type calixarene compound and the hydroxynaphthalene (A) may be dissolved or dispersed in water, or part of the aldehyde (B) may be dissolved or dispersed in the organic solvent.

Next, the reaction system is transferred to a separatory funnel, and the aqueous layer is separated from the organic layer and removed. The organic layer is then washed until a wash (water) becomes neutral. After the washing, the organic layer is left to stand with heating under reduced pressure, and the organic solvent is removed from the organic layer, whereby a naphthol-type calixarene compound with a small amount of residual unreacted monomer (the hydroxynaphthalene (A)) can be obtained.

In place of adding water to the reaction system after the reaction, water may be preliminarily placed in the reaction system. For example, the hydroxynaphthalene (A), an organic solvent, the aldehyde (B), and water are placed, and then an acid catalyst is added with stirring. After the acid catalyst is added, the reaction system is heated to a reaction temperature, and then the hydroxynaphthalene (A) and the aldehyde (B) are allowed to react with stirring, similarly to the reaction system containing no water. The reaction system after the reaction is transferred to a separatory funnel, and similarly to the reaction system containing no water, the organic layer is separated, removed, and neutralized, and then the organic solvent is removed to obtain a naphthol-type calixarene compound.

The naphthol-type calixarene compound obtained may be purified to improve its purity. For example, a crude product obtained by reacting the hydroxynaphthalene (A) with the aldehyde (B) is dissolved in an organic solvent such as methanol, and then the resulting solution is added dropwise to 300 g of ion-exchanged water with stirring and allowed to reprecipitate, whereby a naphthol-type calixarene compound with a purity of 95% or higher in a gel permeation chromatography (GPC) area ratio can be obtained in a yield (a molar ratio of a yield of the naphthol-type calixarene compound to the amount of the hydroxynaphthalene (A) placed in the reaction system) of 50 mol % or higher. The GPC conditions are as described below in EXAMPLES. The reprecipitation can be carried out at room temperature.

As described above, by using not an alkali-metal base catalyst but an acid catalyst, a naphthol-type calixarene compound free from contamination of alkali-metal base catalysts can be produced. Such a naphthol-type calixarene compound free from contamination of metal base catalysts is highly soluble in alkalis and other various solvents and, when dissolved in an organic solvent and applied to a substrate or others, can form a uniform coating.

The naphthol-type calixarene compound according to the present invention provides a coating having high solubility in common organic solvents and high thermal decomposition resistance, and thus can be used in applications including adhesives, paints, photoresists, and various electrical and electronic parts such as printed wiring boards. In particular, the naphthol-type calixarene compound according to the present invention is highly interactive with sensitizers, and thus is suitable as a principal component of a photosensitive composition and provides a resist material having high photosensitivity and resolution. For example, this photosensitive composition, when used in resist applications, can form a resist coating having sufficient thermal decomposition resistance, high photosensitivity, and high resolution, which enables the formation of a fine resist pattern.

The photosensitive composition according to the present invention is characterized by containing a sensitizer in addition to the naphthol-type calixarene compound according to the present invention. When the photosensitive composition according to the present invention is used in the form of a positive resist material, examples of the sensitizer include compounds having a quinone diazide group. When the photosensitive composition according to the present invention is used in the form of a negative resist material, examples include photo acid generators.

Specific examples of the compound having a quinone diazide group include fully esterified compounds, partially esterified compounds, amidated compounds, and partially amidated compounds formed from an aromatic (poly)hydroxy compound and a sulfonic acid having a quinone diazide group, such as naphthoquinone-1,2-diazide-5-sulfonic acid, naphthoquinone-1,2-diazide-4-sulfonic acid, or o-anthraquinone diazide sulfonic acid. These sensitizers may be used alone or in combination.

Examples of the aromatic (poly)hydroxy compound used here include polyhydroxybenzophenone compounds such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, and 2,3,3',4,4',5'-hexahydroxybenzophenone;

bis[(poly)hydroxyphenyl]alkane compounds such as bis(2,4-dihydroxyphenyl)methane, bis(2,3,4-trihydroxyphenylmethane, 2-(4-hydroxyphenyl)-2-(4'-hydroxyphenyl) propane, 2-(2,4-dihydroxyphenyl)-2-(2',4'-dihydroxyphenyl)propane, 2-(2,3,4-trihydroxyphenyl)-2-(2',3',4'-trihydroxyphenyl)propane, 4,4'-{1-[4-[2-(4-hydroxyphenyl)-2-propyl]phenyl]ethylidene}bisphenol, and 3,3'-dimethyl-{1-[4-[2-(3-methyl-4-hydroxyphenyl)-2-propyl]phenyl]ethylidene}bisphenol;

tris(hydroxyphenyl)methane compounds and methyl-substituted products thereof such as tris(4-hydroxyphenyl) methane, bis(4-hydroxy-3,5-dimethylphenyl)-4-hydroxyphenylmethane, bis(4-hydroxy-2,5-dimethylphenyl)-4- hydroxyphenylmethane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-2,5-dimethylphenyl)-3,4-dihydroxyphenylmethane, and bis(4-hydroxy-3,5-dimethylphenyl)-3,4-dihydroxyphenylmethane; and bis(cyclohexylhydroxyphenyl)(hydroxyphenyl)methane compounds and methyl-substituted products thereof such as bis(3-cyclohexyl-4-hydroxyphenyl)-3-hydroxyphenylmethane, bis(3-cyclohexyl-4-hydroxyphenyl)-2-hydroxyphenylmethane, bis(3-cyclohexyl-4-hydroxyphenyl)-4-hydroxyphenylmethane, bis(5-cyclohexyl-4-hydroxy-2-methylphenyl)-2-hydroxyphenylmethane, bis(5-cyclohexyl-4-hydroxy-2-methylphenyl)-3-hydroxyphenylmethane, bis(5-cyclohexyl-4-hydroxy-2-methylphenyl)-4-hydroxyphenylmethane, bis(3-cyclohexyl-2-hydroxyphenyl)-3-hydroxyphenylmethane, bis(5-cyclohexyl-4-hydroxy-3-methylphenyl)-4-hydroxyphenylmethane, bis(5-cyclohexyl-4-hydroxy-3-methylphenyl)-3-hydroxyphenylmethane, bis(5-cyclohexyl-4-hydroxy-3-methylphenyl)-2-hydroxyphenylmethane, bis(3-cyclohexyl-2-hydroxyphenyl)-4-hydroxyphenylmethane, bis(3-cyclohexyl-2-hydroxyphenyl)-2-hydroxyphenylmethane, bis(5-cyclohexyl-2-hydroxy-4-methylphenyl)-2-hydroxyphenylmethane, and bis(5-cyclohexyl-2-hydroxy-4-methylphenyl)-4-hydroxyphenylmethane.

When a compound having a quinone diazide group is used as a sensitizer in the photosensitive composition according to the present invention, the amount of the compound is preferably 5 to 50 parts by mass, more preferably 5 to 30 parts by mass, based on 100 parts by mass of the naphthol-type calixarene compound according to the present invention (in the case where the photosensitive composition according to the present invention contains other resin components: the total solid content of the resin components including the naphthol-type calixarene compound according to the present invention), so as to provide a composition having high photosensitivity.

Examples of the photo acid generator include onium salt compounds, halogen-containing compounds, sulfone compounds, sulfonate compounds, sulfonimide compounds, and diazomethane compounds.

Examples of the onium salt compounds include iodonium salts, sulfonium salts, phosphonium salts, diazonium salts, and pyridinium salts. Specific examples of preferred onium salts include diphenyliodonium trifluoromethanesulfonate, diphenyliodonium p-toluenesulfonate, diphenyliodonium hexafluoroantimonate, diphenyliodonium hexafluorophosphate, diphenyliodonium tetrafluoroborate, triphenylsulfonium triflioromethanesulfonate, triphenylsulfonium p-toluenesulfonate, triphenylsulfonium hexafluoroantimonate, 4-t-butylphenyl.diphenylsulfonium trifluoromethanesulfonate, 4-t-butylphenyl.diphenylsulfonium p-toluenesulfonate, and 4,7-di-n-butoxynaphthyl tetrahydrothiophenium triflioromethanesulfonate.

Examples of the halogen-containing compounds include haloalkyl-containing hydrocarbon compounds and haloalkyl-containing heterocyclic compounds. Specific examples of preferred halogen-containing compounds include 1,10-dibromo-n-decane, 1,1-bis(4-chlorophenyl)-2,2,2-trichloroethane, and s-triazine derivatives such as phenyl-bis(trichloromethyl)-s-triazine, 4-methoxyphenyl-bis(trichloromethyl)-s-triazine, styryl-bis(trichloromethyl)-s-triazine, and naphthyl-bis(trichloromethyl)-s-triazine.

Examples of the sulfone compounds include β-ketosulfone compounds, β-sulfonylsulfone compounds, and α-diazo compounds thereof. Specific examples of preferred sulfone compounds include 4-trisphenacyl sulfone, mesitylphenacyl sulfone, and bis(phenacylsulfonyl)methane.

Examples of the sulfonate compounds include alkyl sulfonic acid esters, haloalkyl sulfonic acid esters, aryl sulfonic acid esters, and iminosulfonates. Specific examples of preferred sulfonate compounds include benzoin tosylate, pyrogallol tristrifluoromethanesulfonate, o-nitrobenzyl trifluoromethanesulfonate, and o-nitrobensyl p-toluenesulfonate.

Examples of the sulfonimide compounds include N-(trifluoromethylsulfonyloxy)succinimide, N-(trifluoromethylsulfonyloxy)phthalimide, N-(trifluoromethylsulfonyloxy)diphenylmaleimide, N-trifluoromethylsulfonyloxy)bicyclo[2.2.1]hept-5-ene-2,3-dicarboxyimide, and N-(trifluoromethylsulfonyloxy)naphthylimide.

Examples of the diazomethane compounds include bis(trifluoromethylsulfonyl)diazomethane, bis(cyclohexylsulfonyl)diazomethane, and bis(phenylsulfonyl)diazomethane.

When a photo acid generator is used as a sensitizer in the photosensitive composition according to the present invention, the amount of the generator is preferably 5 to 50 parts by mass, more preferably 5 to 30 parts by mass, based on 100 parts by mass of the naphthol-type calixarene compound according to the present invention (in the case where the photosensitive composition according to the present invention contains other resin components: the total solid content of the resin components including the naphthol-type calixarene compound according to the present invention), so as to provide a composition having high photosensitivity.

In the photosensitive composition according to the present invention, other resin components may be used in combination in addition to the naphthol-type calixarene compound according to the present invention. Preferred other resins are those which are soluble in alkali developers, or those which are dissolved in alkali developers when used in combination with additives such as acid generators (alkali-soluble resins).

Examples of the other resins used here include various novolac resins, resins formed by the addition polymerization of an alicyclic diene compound, such as dicyclopentadiene, and a phenol compound, modified novolac resins formed from a phenolic hydroxyl-containing compound and an alkoxy-containing aromatic compound, phenol aralkyl resins (xylok resins), naphthol aralkyl resins, trimethylolmethane resins, tetraphenylol ethane resins, biphenyl-modified phenol resins, biphenyl-modified naphthol resins, aminotriazine-modified phenol resins, and various vinyl polymers.

More specifically, the various novolac resins include polymers obtained by reacting phenolic hydroxyl-containing compounds, such as phenolenol, alkylphenols (e.g., cresol and xylenol), phenylphenol, resorcinol, biphenyl, bisphenols (e.g., bisphenol A and bisphenol F), naphthol, and dihydroxynaphthalene, with aldehyde compounds under acid catalytic conditions.

Examples of the various vinyl polymers include homopolymers of vinyl compounds such as polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, and poly(meth)acrylate; and copolymers thereof.

When the above-described other resins are used, the blending ratio of the naphthol-type calixarene compound according to the present invention to the other resins can be freely determined according to the intended use. In particular, the naphthol-type calixarene compound according to the present invention is preferably used in an amount of 60% by mass or more, more preferably 80% by mass or more, based on the total amount of the naphthol-type calixarene compound according to the present invention and the other resins, so as to sufficiently produce the effects of the present invention, i.e., high photosensitivity, resolution, and thermal decomposition resistance.

The photosensitive composition according to the present invention may contain a surfactant in order, for example, to exhibit improved film formability and pattern adhesion and suffer from reduced development defects when used in resist applications. Examples of the surfactant used here include nonionic surfactants including polyoxyethylene alkyl ether compounds such as polyoxyethylene lauryl ether, polyoxyethylene stearyl ether, polyoxyethylene cetyl ether, and polyoxyethylene oleyl ether, polyoxyethylene alkylallyl ether compounds such as polyoxyethylene octylphenol ether and polyoxyethylene nonylphenol ether, polyoxyethylene-.polyoxypropylene block copolymers, sorbitan fatty acid ester compounds such as sorbitan monolaurate, sorbitan monopalmitate, sorbitan monostearate, sorbitan monooleate, sorbitan trioleate, and sorbitan tristearate, and polyoxyethylene sorbitan fatty acid ester compounds such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants having fluorine atoms in their molecular structures, such as copolymers of fluoroaliphatic group-containing polymerizable monomers and [poly(oxyalkylene)](meth)acrylates; and silicone surfactants having silicone-structured moieties in their molecular structures. These may be used alone or in combination. The amount of such a surfactant for use is preferably in the range of 0.001 to 2 parts by mass based on 100 parts by mass of the resin solids (including the naphthol-type calixarene compound according to the present invention) in the photosensitive composition according to the present invention.

The photosensitive composition according to the present invention may further contain a filler. The filler can provide a coating with improved hardness and thermal decomposition resistance. The filler contained in the photosensitive composition according to the present invention may be an organic filler, and is preferably an inorganic filler. Examples of the inorganic filler include silica, mica, talc, clay, bentonite, montmorillonite, kaolinite, wollastonite, calcium carbonate, calcium hydroxide, magnesium carbonate, titanium oxide, alumina, aluminum hydroxide, barium sulfate, barium titanate, potassium titanate, zinc oxide, and glass fibers. Of these, silica, which can reduce the coefficient of thermal expansion, is suitable for use.

The photosensitive composition according to the present invention contains the naphthol-type calixarene compound according to the present invention and a sensitizer as essential components, and may optionally, but not necessarily, contains a curing agent.

Examples of the curing agent for use in the present invention include melamine compounds substituted with at least one group selected from methylol, alkoxymethyl, and acyloxymethyl, guanamine compounds, glycoluril compounds, urea compounds, resol resins, epoxy compounds, isocyanate compounds, azide compounds, compounds having double bonds such as alkenyl ether groups, acid anhydrides, and oxazoline compounds.

Examples of the melamine compounds include hexamethylol melamine, hexamethoxymethyl melamine, hexamethylol melamine derivatives in which 1 to 6 methylol groups are methoxymethylated, hexamethoxyethyl melamine, hexaacyloxymethyl melamine, and hexamethylol melamine derivatives in which 1 to 6 methylol groups are acyloxymethylated.

Examples of the guanamine compounds include tetramethylol guanamine, tetramethoxymethyl guanamine, tetramethoxymethyl benzoguanamine, tetramethylol guanamine derivatives in which 1 to 4 methylol groups are methoxymethylated, tetramethoxyethyl guanamine, tetraacyloxy guanamine, and tetramethylol guanamine derivatives in which 1 to 4 methylol groups are acyloxymethylated.

Examples of the glycoluril compounds include 1,3,4,6-tetrakis(methoxymethyl) glycoluril, 1,3,4,6-tetrakis(butoxymethyl) glycoluril, and 1,3,4,6-tetrakis(hydroxymethyl) glycoluril.

Examples of the urea compounds include 1,3-bis(hydroxymethyl)urea, 1,1,3,3-tetrakis(butoxymethyl)urea, and 1,1,3,3-tetrakis(methoxymethyl)urea.

Examples of the resol resins include polymers obtained by reacting phenolic hydroxyl-containing compounds, such as phenol, alkylphenols (e.g., cresol and xylenol), phenylphenol, resorcinol, biphenyl, bisphenols (e.g., bisphenol A and bisphenol F), naphthol, and dihydroxynaphthalene, with aldehyde compounds under alkaline catalytic conditions.

Examples of the epoxy compounds include tris(2,3-epoxypropyl) isocyanurate, trimethylolmethane triglycidyl ether, trimethylolpropane triglycidyl ether, and triethylolethane triglycidyl ether.

Examples of the isocyanate compounds include tolylene diisocyanate, diphenylmethane diisocyanate, hexamethylene diisocyanate, and cyclohexane diisocyanate.

Examples of the azide compounds include 1,1'-biphenyl-4,4''-bisazide, 4,4'-methylidene bisazide, and 4,4'-oxybisazide.

Examples of the compounds having double bonds such as alkenyl ether groups include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

Examples of the acid anhydrides include aromatic acid anhydrides such as phthalic anhydride, trimellitic anhydride, pyromellitic dianhydride, 3,3',4,4'-benzophenonetetracarboxylic dianhydride, biphenyltetracarboxylic dianhydride, 4,4'-(isopropylidene)diphthalic anhydride, and 4,4'-(hexafluoroisopropylidene)diphthalic anhydride; and alicyclic carboxylic anhydrides such as tetrahydrophthalic anhydride, methyltetrahydrophthalic anhydride, hexahydrophthalic anhydride, methylhexahydrophthalic anhydride, endomethylene tetrahydrophthalic anhydride dodecenylsuccinic anhydride, and trialkyltetrahydrophthalic anhydride.

Of these, preferred are glycoluril compounds, urea compounds, and resol resins, which have excellent curing properties and provide compositions that provide films that exhibit high dry etching resistance and thermal decomposition resistance when used as resist underlayer films or permanent films, and particularly preferred are glycoluril compounds.

When the photosensitive composition according to the present invention contains such a curing agent, the amount of the curing agent is 50 parts by mass or less based on 100 parts by mass of the naphthol-type calixarene compound according to the present invention so as to maintain the high sensitivity provided by the naphthol-type calixarene compound according to the present invention. The amount of the curing agent in the photosensitive composition according to the present invention is preferably 0.1 to 50 parts by mass based on 100 parts by mass of the naphthol-type calixarene compound according to the present invention so as to provide a composition that provides a film having high curability, thermal decomposition resistance, and alkali developability, and more preferably 0.1 to 30 parts by mass, still more preferably 0.5 to 20 parts by mass, so as to provide a composition that provides a film also having high photosensitivity.

The photosensitive composition according to the present invention is preferably an organic solvent solution or dispersion of the naphthol-type calixarene compound according to the present invention and various optional additives such as other resins, a sensitizer, a surfactant, a filler, a curing agent, a photo acid generator, an organic base compound, a dye, a pigment, a cross-linking agent, and a dissolution promoter. Applying the organic solvent solution or dispersion to a substrate or others can form a coating. The photo acid generator, organic base compound, dye, pigment, cross-linking agent, and dissolution promoter for use can be appropriately selected depending on the intended use from those which are commonly used as additives for resist materials.

Examples of the organic solvent include alkylene glycol monoalkyl ethers such as ethylene glycol monomethyl ether, ethylene glycol monoethyl ether, ethylene glycol monopropyl ether, and ethylene glycol monobutyl ether propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; alkylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate. These may be used alone or in combination.

The photosensitive composition according to the present invention can be prepared by blending the above-described components and mixing them by using, for example, a stirrer. When the photosensitive composition contains a filler or a pigment, the photosensitive composition can be prepared by dispersing or mixing the components by using a dispersing device such as a dissolver, a homogenizer, or a triple roll mill.

The photosensitive composition according to the present invention is suitable for use as a resist material. The photosensitive composition according to the present invention may be used as a resist material in the form of a solution/dispersion in an organic solvent, or may be used in the form of a resist film formed by applying a solution/dispersion in an organic solvent into a film and removing the solvent. When the photosensitive composition is used in the form of a resist film, examples of support films include plastic films of polyethylene, polypropylene, polycarbonate, and polyethylene terephthalate, and the support film may be a monolayer film or a laminated multilayer film. The surface of the support film may be corona treated or provided with a release agent.

Photolithography using the photosensitive composition according to the present invention is performed as follows, for example. A solution/dispersion of the photosensitive composition (resist material) in an organic solvent is applied to an object to be subjected to silicon substrate photolithography, and pre-baked at a temperature of 60° C. to 150° C. The application can be carried out by any method such as spin coating, roll coating, flow coating, dip coating, spray coating, or doctor blade coating. Next, a resist pattern is formed. When the photosensitive composition is positive, a target resist pattern is exposed to light through a predetermined mask, and the exposed area is dissolved with an alkali developer to form a resist pattern. The photosensitive composition according to the present invention, for its high photosensitivity, can form a resist pattern having high resolution.

Examples of the exposure source used here include infrared light, visible light, ultraviolet light, far-ultraviolet light, X-rays, and electron beams, and the ultraviolet light includes g-line (wavelength: 436 nm), h-line (wavelength: 405 nm), and i-line (wavelength: 365 nm) from a high-pressure mercury lamp; and KrF excimer laser light (wavelength: 248 nm), ArF excimer laser light (wavelength: 193 nm), F2 excimer laser light (wavelength: 157 nm), and EUV laser light (wavelength: 13.5 nm). The photosensitive composition according to the present invention, for its high photosensitivity and alkali developability, can form a resist pattern having high resolution when any light source is used.

The naphthol-type calixarene compound according to the present invention has high stiffness due to having a calixarene structure including more than one naphthalene ring structure. The naphthol-type calixarene compound, when used for a resist underlayer film, provides high resistance to dry etching using halogen plasma gas and other gas and high thermal decomposition resistance. In addition, such a compound that includes numbers of naphthalene ring structures has a high refractive index and high absorbance, and thus has low light reflectance when cured. Therefore, the naphthol-type calixarene compound according to the present invention is a material also suitable as a resist underlayer film material.

Since the naphthol-type calixarene compound according to the present invention has high thermal decomposition resistance, a thin film (e.g., a resist coating) made of a photosensitive composition containing a major proportion of the naphthol-type calixarene compound is suitable as a permanent film, which will be left in an end product, optionally, after a resist pattern is formed. Products having a gap between members may be deformed due to a difference in thermal expansion between the member side and the gap side of a permanent film, but a permanent film made of a photosensitive composition containing a major proportion of the naphthol-type calixarene compound according to the present invention is advantageously less likely to undergo such deformation.

It is to be noted that the permanent film is a coating made of a photosensitive composition and formed on or between parts of products, mainly, semiconductor devices such as ICs and LSIs and display devices such as flat displays, and the coating is left after the products are finished. Specific examples of the permanent film include solder resists, package materials, underfill materials, package bonding layers for circuit elements and for others, and layers for bonding integrated circuit elements to circuit boards, which are related to semiconductor devices; and thin-film transistor protective films, liquid crystal color filter protective films, black matrices, and spacers, which are related to flat displays typified by LCDs and OELDs.

The naphthol-type calixarene compound according to the present invention, which has a calixarene structure, has an inclusion function and a catalytic function due to the structure. Having such advantageous functions, the naphthol-type calixarene compound is expected to find use, for example, in qualitative and quantitative analyses of metal ions, separation of metal ions, molecular sensors, synthetic enzymes, various chromatography materials, and charge control agents for toner.

EXAMPLES

The present invention will now be described in more detail with reference to examples, but these examples are not intended to limit the present invention. "Parts" and "%" given below are by mass unless otherwise specified.

<Measurement of Resin>

The molecular weight distribution of resins (including the naphthol-type calixarene compound according to the present invention) was measured by GPC using the polystyrene standard method under the following measurement conditions.

(Measurement Conditions of GPC)
Apparatus: "HLC-8220 GPC" available from Tosoh Corporation
Column: "Shodex KF802" (8.0 mm I.D.×300 mm) available from Showa Denko K.K.
  "Shodex KF802" (8.0 mm I.D.×300 mm) available from Showa Denko K.K.
  "Shodex KF803" (8.0 mm I.D.×300 mm) available from Showa Denko K.K.
  "Shodex KF804" (8.0 mm I.D.×300 mm) available from Showa Denko K.K.
Detector: ELSD ("ELSD2000" available from Alltech Japan)
Data Processing: "GPC-8020 Model II data analysis version 4.30" available from Tosoh Corporation
Measurement Conditions:
  Column temperature, 40° C.
  Developing solvent, tetrahydrofuran (THF)
  Flow rate, 1.0 mL/min
Sample: prepared by filtering a tetrahydrofuran solution in an amount of 1.0% by mass on a resin solids basis through a microfilter (5 μL),
Standard sample: in accordance with a measurement manual of "GPC-8020 Model II data analysis version 4.30", the following monodisperse polystyrenes of known molecular weight we re used.
(Monodisperse Polystyrene)
  "A-500" available from Tosoh Corporation
  "A-1000" available from Tosoh Corporation
  "A-2500" available from Tosoh Corporation
  "A-5000" available from Tosoh Corporation
  "F-1" available from Tosoh Corporation
  "F-2" available from Tosoh Corporation
  "F-4" available from Tosoh Corporation
  "F-10" available from Tosoh Corporation
  "F-20" available from Tosoh Corporation
  "F-40" available from Tosoh Corporation
  "F-80" available from Tosoh Corporation
  "F-128" available from Tosoh Corporation
  "F-288" available from Tosoh Corporation
  "F-550" available from Tosoh Corporation Conditions for Measuring FD-MS Spectrum>
The FD-MS spectrum of resins (including the naphthol-type calixarene compound according to the present invention) was measured using an "AX505H (FD505H)" double-focusing mass spectrometer available from JEOL Ltd,

[Example 1] <Naphthol-Type Calixarene Compound 1>

Figure 1:
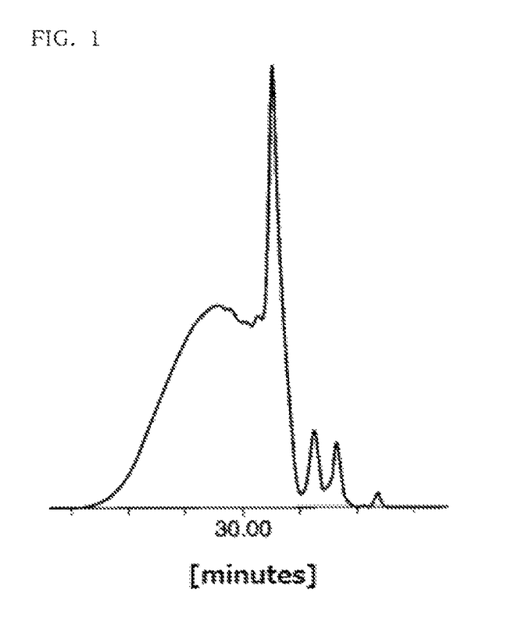
FIG. 1 is a GPC chart of a mixture (1) obtained in SYNTHESIS EXAMPLE 1.

In a flask equipped with a thermometer, a dropping funnel, a condenser, and a stirrer, 288 g of 1-naphthol, 107 g of paraldehyde, 500 g of 2-ethoxyethanol, and 5.8 g of 95% sulfuric acid were placed, heated to 80° C., and then stirred for 10 hours. After completion of the reaction, 300 g of ethyl acetate and 160 g of ion-exchanged water were added, and then using a separatory funnel, an aqueous layer having a pH of 1 at a lower layer was disposed of. The washing of an organic layer with 160 g of ion-exchanged water was carried out seven times, at which time the aqueous layer disposed of had a pH of 4. Using an evaporator, the organic layer at an upper layer was concentrated by heating under reduced pressure and dried to provide 309 g of a mixture (1) containing the desired compound represented by the above general formula (1) wherein n is 4, $R^1$ is a hydrogen atom, and $R^2$ is a methyl group, in a GPC area ratio of 18%. The yield was 91%, and a peak at 680, which indicates a cyclic compound, was observed in an FD-MS spectrum. A GPC spectrum of the mixture (1) obtained is shown in FIG. 1.

[Example 2] <Naphthol-Type Calixarene Compound 2>

Figure 2:
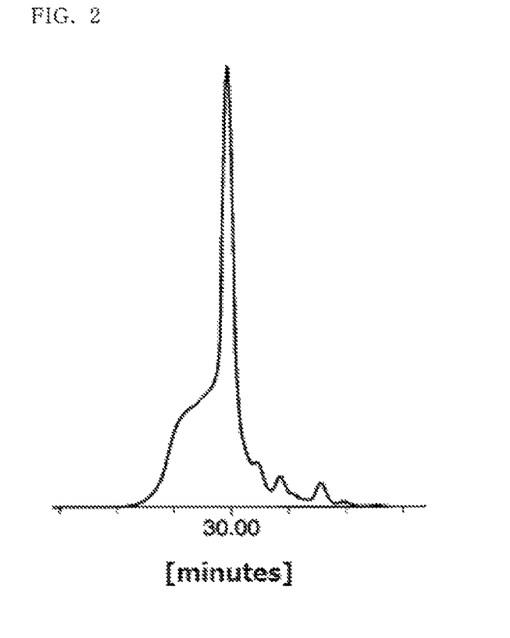
FIG. 2 is a GPC chart of a mixture (2) obtained in SYNTHESIS EXAMPLE 2.

In a flask equipped with a thermometer, a dropping funnel, a condenser, and a stirrer, 288 g of 1-naphthol, 244 g of 4-hydroxybenzaldehyde, 500 g of 1-butanol, and 14.4 g of 95% sulfuric acid were placed, heated to 80° C., and then stirred for 17 hours. After completion of the reaction, 300 g of ethyl acetate and 160 g of ion-exchanged water were added, and then using a separatory funnel, an aqueous layer having a pH of 1 at a lower layer was disposed of. The washing of an organic layer with 160 g of ion-exchanged water was carried out seven times, at which time the aqueous layer disposed of had a pH of 4. Using an evaporator, the organic layer at an upper layer was concentrated by heating under reduced pressure and dried to provide 466 g of a mixture (2) containing the desired compound represented by the above general formula (1) wherein n is 4, $R^1$ is a hydrogen atom, and $R^2$ is a hydroxyphenyl group, in a GPC area ratio of 52%. The yield was 94%, and a peak at 992, which indicates a cyclic compound, was observed in an FD-MS spectrum. A GPC spectrum of the mixture (2) obtained is shown in FIG. 2.

[Comparative Example 1] <Cyclic Compound of 1-Naphthol and Formaldehyde>

In a flask equipped with a thermometer, a dropping funnel, a condenser, and a stirrer, 48 g of α-naphthol, 26 g of a 42% by mass aqueous formaldehyde solution, 50 g of isopropyl alcohol, and 9.4 g of 48% sodium hydroxide were placed and stirred at room temperature under a stream of nitrogen. The resulting mixture was then heated to 80° C. and stirred for 1 hour. After completion of the reaction, the resultant was neutralized by adding 8 g of primary sodium phosphate and cooled, and crystals were separated by filtration. The crystals were washed with 50 g of water three times and then dried by heating under reduced pressure to provide 47 g a comparative mixture (1').

[Comparative Example 2] <Reaction Product of 1-Naphthol and Formaldehyde>

In a 1 L four-necked flask equipped with a thermometer, a condenser, and a stirrer, 144 g of 1-naphthol, 400 g of methyl isobutyl ketone, 96 g of water, and 27.7 g of 92% paraformaldehyde were placed. Subsequently, 4.8 g of an aqueous p-toluenesulfonic acid solution, the concentration of which was adjusted to 50%, was added with stirring. The resulting mixture was then heated to 80° C. with stirring and allowed of react for 2 hours. After completion of the reaction, the solution of the system was transferred to a separatory funnel, and the aqueous layer was separated from the organic layer and removed. Next, after being washed with water until the washing water became neutral, the organic layer was desolvated with heating under reduced pressure to provide 147 g of a comparative novolac resin (2').

[Examples 3 to 4, Comparative Examples 3 to 4]

Using the mixtures (1) to (2), the comparative mixture (1'), and the comparative novolac resin (2'), synthesized in EXAMPLES 1 to 2 and COMPARATIVE EXAMPLES 1 to 2, the resin component, a sensitizer ["P-200" available from Toyo Gosei Co., Ltd., a condensate of 4,4'-[1-[4-[1-(4-hydroxyphenyl)-1 methylethyl]phenyl]ethylidene]bisphenol (1 mol) and 1,2-naphthoquinone-2-diazide-5-sulfonyl chloride (2 mol)], and propylene glycol monomethyl ether acetate (hereinafter referred to as "PGMEA" from short) were mixed in a ratio of 16/4/80 (parts by mass), as shown in Table 1, and dissolved. The resulting mixtures were then each filtered through a 0.2 µm membrane filter to provide photosensitive compositions (positive resist compositions).

The positive photosensitive compositions obtained were evaluated for solvent solubility, and coatings obtained by using these compositions were evaluated for alkali developability, sensitivity, resolution, and thermal decomposition resistance. The evaluation methods are as described below.

<Solvent Solubility>

Into a sample jar, 8 g of each compound (or resin) synthesized in SYNTHESIS EXAMPLES 1 to 2 and Comparative SYNTHESIS EXAMPLES 1 to 2, 2 g of a sensitizer (P-200), and PGMEA were added to a solution concentration of 20% and then stirred at normal temperature with a shaker. After the stirring, the state of the solvent in the sample jar was visually evaluated. The evaluation criteria were as follows: uniform and transparent, "good"; solids precipitated or sedimented, "poor".

<Evaluation of Alkali Developability>

The photosensitive composition was applied to a 5-inch silicon wafer to a thickness of about 1 µm with a spin coater and dried on a hot plate at 110° C. for 60 seconds to provide a silicon wafer having a coating. The wafer obtained was immersed is an alkali developer (2.38% aqueous tetramethylammonium hydroxide solution) for 60 seconds and then dried on a hot plate at 110° C. for 60 seconds. The thickness of the coating of the photosensitive composition was measured before and after the immersion in the developing solution, and a value obtained by dividing the difference by 60 was used as an evaluation result of alkali developability (ADR (nm/s)). When the wafer was exposed to light, the wafer was irradiated by a ghi line lamp (Multi Light available from USHIO INC.) at 100 mJ/cm², at which sufficient exposure was achieved, and then subjected to post exposure bake (PEB) at 140° C. for 60 seconds; the wafer thus obtained was used to evaluate ADR alkali developability.

<Evaluation of Sensitivity>

On the 5-inch silicon wafer having a coating formed by applying the photosensitive composition to a thickness of 1 µm and drying the composition, a mask for 1 to 10 µm resist patterns of 1:1 line-and-space was put in close contact, and then the amount of exposure (the amount of Eop exposure) that can faithfully reproduce 3 µm with a ghi line lamp was determined, <Evaluation of Resolution>

A photomask was placed on the 5-inch silicon wafer having a coating formed by applying and drying the photosensitive composition, and exposed to light by irradiation by a ghi line lamp (Multi Light available from USHIO INC.) at 100 mJ/cm2. The coating after the irradiation was developed and dried in the same manner as in Evaluation of Alkali Developability. The state of the resist pattern on the wafer after development was evaluated using a laser microscope (VK-8500) available from Keyence Corporation. The evaluation criteria were as follows: resolved at L/S=3 µm, "good"; not resolved at L/S=3 µm, "poor".

<Evaluation of Thermal Decomposition Resistance>

The photosensitive composition was applied to a 5-inch silicon wafer to a thickness of 1 µm with a spin coater and dried on a hot plate at 110° C. for 60 seconds to provide a silicon wafer having a coating. The resin was scraped off of the wafer obtained, and Tg was measured. The measurement of Tg was conducted using a differential thermal-thermogravimetric analyzer (product name: TG/DTA 6200, available from Seiko Instruments Inc.) in a nitrogen atmosphere under the following conditions: temperature range, room temperature to 400° C.; heating rate, 10° C./min. The weight loss during the heating at a constant rate was measured to determine a thermal decomposition onset temperature.

TABLE 1

|  | Example 3 | Example 4 | Comparative Example 3 | Comparative Example 4 |
| --- | --- | --- | --- | --- |
| Mixture (1) | 16 | — | — | — |
| Mixture (2) | — | 16 | — | — |
| Comparative mixture (1') | — | — | 16 | — |
| Comparative novolac resin (2') | — | — | — | 16 |
| Sensitizer | 4 | 4 | 4 | 4 |
| PGMEA | 80 | 80 | 80 | 80 |
| Total | 100 | 100 | 100 | 100 |
| Evaluation | | | | |
| Solvent Solubility | Good | Good | Poor | Good |
| ADR (nm/s) pre-exposure | 0 | 0 | — | 0 |
| post-exposure | 1,270 | >5,000 | — | 1,130 |
| Sensitivity (mJ/cm²) | 40 | 40 | — | 60 |
| Resolution | Good | Good | — | Poor |
| Thermal decomposition onset temperature (° C.) | >200 | >200 | >200 | >200 |

The results showed that the mixtures (1) to (2), containing the naphthol-type calixarene compound according to the present invention, had good solubility in PGMEA, whereas the comparative mixture (1'), which was synthesized using sodium hydroxide as a catalyst, was not completely dissolved in PGMEA and left as a precipitate. Thus, for the photosensitive composition containing the comparative mixture (1') (COMPARATIVE EXAMPLE 3), alkali dissolution rate and resolution were not evaluated, and a data of thermal decomposition onset temperature alone was acquired.

The coatings made of the photosensitive compositions containing the mixtures (1) to (2) (EXAMPLES 3 to 4) had good post-exposure ADR of not less than 1,200 nm/s, high photosensitivity and resolution, and a sufficiently high thermal decomposition onset temperatures of 200° C. or higher, indicating good thermal decomposition resistance. By contrast, the coating made of the photosensitive composition containing the comparative novolac resin (2') (COMPARATIVE EXAMPLE 4) had good thermal decomposition resistance but poorer ADR and sensitivity compared with EXAMPLES 3 to 4.

[Examples 5 to 6, Comparative Examples 5 to 6]

The photosensitive compositions according to the present invention were evaluated assuming the use for resist permanent films.

Specifically, using the mixtures (1) to (2), the comparative mixture (1'), and the comparative novolac resin (2'), synthesized in EXAMPLES 1 to 2 and COMPARATIVE EXAMPLES 1 to 2, the resin component, a sensitizer ["P-200" available from Toyo Gosei Co., Ltd., a condensate of 4,4'-[1-[4-[1-(4-hydroxyphenyl)-1methylethyl]phenyl] ethylidene]bisphenol (1 mol) and 1,2-naphthoquinone-2-diazide-5-sulfonyl chloride (2 mol)], a cross-linking agent [1,3,4,6-tetrakis(methoxymethyl) glycoluril available from Tokyo Chemical Industry Co., Ltd.], and PGMEA were mixed in a ratio of 16/3/1/80 (parts by mass), as shown in Table 2, and dissolved. The resulting mixtures were then each filtered through a 0.2 μm membrane filter to provide photosensitive compositions (photoresist permanent film compositions).

The photoresist permanent film compositions obtained were evaluated for solvent solubility, and coatings obtained by using these compositions were evaluated for alkali developability, sensitivity, resolution, and thermal decomposition resistance. The evaluation methods are as described below. The results are shown in Table 2.

<Evaluation of Solvent Solubility>
The evaluation was made in accordance with the method described above in Evaluation of Solvent Solubility.

<Evaluation of Alkali Developability>
The evaluation was made in accordance with the method described above in Evaluation of Alkali Developability.

<Evaluation of Sensitivity>
The evaluation was made in accordance with the method described above in Evaluation of Sensitivity.

<Evaluation of Resolution>
A photomask was placed on the 5-inch silicon wafer having a coating formed by applying and drying the photosensitive composition, and exposed to light by irradiation by a ghi line lamp (Multi Light available from USHIO INC.) at 100 mJ/cm2. The coating after the irradiation was developed and dried in the same manner as in Evaluation of Alkali Developability. The state of the resist pattern on the wafer after development was evaluated using a laser microscope (VK-8500) available from Keyence Corporation. Assuming the use for resist permanent films, the evaluation criteria were as follows: resolved at L/S=5 μm, "good"; not resolved at L/S=5 μm, "poor".

<Thermal Decomposition Resistance>
The evaluation was made in accordance with the method described above in Evaluation of Thermal Decomposition Resistance.

TABLE 2

|  | Example 5 | Example 6 | Comparative Example 5 | Comparative Example 6 |
|---|---|---|---|---|
| Mixture (1) | 16 | — | — | — |
| Mixture (2) | — | 16 | — | — |
| Comparative mixture (1') | — | — | 16 | — |
| Comparative novolac resin (2') | — | — | — | 16 |
| Sensitizer | 3 | 3 | 3 | 3 |
| Cross-linking agent | 1 | 1 | 1 | 1 |
| PGMEA | 80 | 80 | 80 | 80 |
| Total | 100 | 100 | 100 | 100 |
| Evaluation | | | | |
| Solvent Solubility | Good | Good | Poor | Good |
| ADR (nm/s) pre-exposure | 0 | 0 | — | 0 |
| post-exposure | 1,270 | >5,000 | — | 1,130 |
| Sensitivity (mJ/cm$^2$) | 40 | 40 | — | 60 |
| Resolution | Good | Good | — | Poor |
| Thermal decomposition onset temperature (° C.) | >200 | >200 | >200 | >200 |

The coatings made of the photosensitive compositions containing the mixtures (1) to (2) (EXAMPLES 5 to 6) were resolved at L/S=5 μm and had good thermal decomposition resistance, photosensitivity, and resolution, suggesting that these coatings are suitable as resist permanent films.

The invention claimed is:

1. A positive type photosensitive resist composition comprising:
    a sensitizer; and
    a naphthol-type calixarene compound obtained by reacting a hydroxynaphthalene (A) with an aldehyde (B) represented by formula (3) in the presence of an acid catalyst:

$R^2$—CHO  (3)

$R^2$ represents an optionally substituted alkyl group or an optionally substituted aryl group,
        wherein a layer exposed to light of the positive type photosensitive resist composition has an alkali developability.

2. A coating comprising the positive type photosensitive resist composition according to claim 1.

3. The positive type photosensitive resist composition according to claim 1, wherein the hydroxynaphthalene (A) is represented by general formula (2):

(2)

wherein in the general formula (2), $R^1$ represents a hydrogen atom, an alkyl group, an optionally substituted aryl group, an optionally substituted aralkyl group or a halogen atom, in which a plurality of $R^1$ may be the same or different from each other.

4. The positive type photosensitive resist composition according to claim 3, wherein the naphthol-type calixarene compound is represented by general formula (1-1):

(1-1)

wherein $R^1$ is defined in the formula (2), $R^2$ is defined in the formula (3), and n represents an integer of 2 to 10.

5. The positive type photosensitive resist composition according to claim 3, wherein $R^2$ is a methyl group or a hydroxyphenyl group.

* * * * *